United States Patent
Chang et al.

(10) Patent No.: US 9,433,739 B2
(45) Date of Patent: Sep. 6, 2016

(54) INNER TYPE TRACHEOSTOMY TUBE

(71) Applicant: VITALTEC CORPORATION, Taichung (TW)

(72) Inventors: Ti-Li Chang, Taichung (TW); Sheng-Yu Chiu, Taichung (TW)

(73) Assignee: Vitaltec Corporation, Taichung Hsien (TW)

( * ) Notice: Subject to any disclaimer, the term of this patent is extended or adjusted under 35 U.S.C. 154(b) by 319 days.

(21) Appl. No.: 13/912,343

(22) Filed: Jun. 7, 2013

(65) Prior Publication Data
US 2013/0269690 A1    Oct. 17, 2013

Related U.S. Application Data

(63) Continuation-in-part of application No. 12/899,624, filed on Oct. 7, 2010, now abandoned.

(51) Int. Cl.
*A61M 16/00* (2006.01)
*A62B 9/02* (2006.01)
*A61M 16/04* (2006.01)

(52) U.S. Cl.
CPC ..... *A61M 16/0488* (2013.01); *A61M 16/0427* (2014.02); *A61M 16/0465* (2013.01); *A61M 16/0497* (2013.01); *A61M 16/0434* (2013.01)

(58) Field of Classification Search
None
See application file for complete search history.

(56) References Cited

U.S. PATENT DOCUMENTS

| | | | | |
|---|---|---|---|---|
| 4,009,720 A | * | 3/1977 | Crandall | A61M 16/0465 128/207.15 |
| 4,033,353 A | * | 7/1977 | La Rosa | 128/207.15 |
| 6,105,577 A | * | 8/2000 | Varner | A61M 16/0465 128/207.14 |
| 6,248,099 B1 | * | 6/2001 | Bell | 604/533 |
| 6,668,825 B2 | | 12/2003 | Cardon | |
| 7,435,214 B2 | * | 10/2008 | Kucklick et al. | 600/125 |
| 2007/0083262 A1 | * | 4/2007 | Matlock | A61M 16/0465 623/9 |
| 2007/0144526 A1 | * | 6/2007 | Blom et al. | 128/207.16 |
| 2007/0181132 A1 | * | 8/2007 | Worley | 128/207.14 |
| 2009/0095302 A1 | * | 4/2009 | Blom | 128/207.16 |
| 2009/0156953 A1 | * | 6/2009 | Wondka | A61M 16/0465 600/538 |
| 2010/0108076 A1 | * | 5/2010 | Chang | 128/207.17 |
| 2011/0083672 A1 | * | 4/2011 | Webster | A61M 16/0465 128/207.15 |
| 2011/0139151 A1 | * | 6/2011 | Burns | A61M 16/04 128/203.12 |
| 2012/0048277 A1 | * | 3/2012 | Waldron | A61M 16/0488 128/207.14 |
| 2012/0066330 A1 | * | 3/2012 | Fan | H04L 12/1859 709/206 |

* cited by examiner

*Primary Examiner* — Jason Flick
*Assistant Examiner* — Eric Bryant
(74) *Attorney, Agent, or Firm* — Alan D. Kamrath; Kamrath IP Lawfirm, P.A.

(57) ABSTRACT

An inner type tracheostomy tube has an outer tube and an inner cannula. The outer tube has an airway tube, an inflatable cuff and an inflating tube. The inner cannula is connected to the outer tube and has an inner tube, a disk segment, a connecting mount and a connector. The connecting mount is soft and bendable, is securely mounted around the disk segment and has a bottom end, a top end and a flange coat. The bottom end is securely mounted around the disk segment and has an inner surface and an air gap formed between the inner surface of the bottom end of the connecting mount and the disk segment. The connector is securely mounted around the top end of the connecting mount and has a bottom end and a flange formed around the bottom end of the connector and enclosed by the flange coat.

10 Claims, 7 Drawing Sheets

INNER TYPE TRACHEOSTOMY TUBE

The present invention is a continuation-in-part of application Ser. No. 12/899,624, filed on Oct. 7, 2010, now abandoned.

BACKGROUND OF THE INVENTION

1. Field of the Invention

The present invention relates to an inner type tracheostomy tube and, more particularly, to an inner type tracheostomy tube that can easily and safely change an inner cannula of the inner type tracheostomy tube.

2. Description of Related Art

A patient who has dyspnea due to trachea obstruction or disease caused by weakness or drug effects may require a conventional tracheostomy tube inserted into the trachea through a stoma formed through the trachea to provide air from a respiratory tube directly to the patient through the conventional tracheostomy tube.

When changing the conventional tracheostomy tube, a surgical operation is needed to inconveniently operate on the patient under a general anesthesia. A conventional inner type tracheostomy tube can be used to improve the aforementioned problem and has an outer tube and an inner cannula. The inner cannula is connected to the outer tube by screwing or clamping. Thus, the inner cannula of the conventional inner type tracheostomy tube can be changed from the outer tube to improve the convenience of using the conventional tracheostomy tube.

However, the inner cannula of the conventional inner type tracheostomy tube is screwed with the outer tube and may be separated from the outer tube when the inner cannula is rotated with a respiratory tub, and this is dangerous in use. Furthermore, when the inner cannula of the conventional inner type tracheostomy tube is connected to the outer tube by an exerted clamping structure, dirt may be accumulated on the exerted clamping structure causing infection. In addition, the patent may knock the exerted clamping structure of the inner cannula to cause the inner cannula to separate from the outer tub, and this is unsafe in use.

To overcome the shortcomings, the present invention provides an inner type tracheostomy tube to mitigate or obviate the aforementioned problems.

SUMMARY OF THE INVENTION

The main objective of the present invention is to provide an inner type tracheostomy tube that can easily and safely change an inner cannula of the inner type tracheostomy tube.

The inner type tracheostomy tube in accordance with the present invention has an outer tube and an inner cannula. The outer tube has an airway tube, an inflatable cuff and an inflating tube. The inflatable cuff is mounted around an inner end of the airway tube. The inflating tube is connected to and communicates with the inflatable cuff. The inner cannula is detachably connected to the outer tube and has an inner tube, a disk segment, a connecting mount and a connector. The disk segment is formed on the external surface of the inner tube at the outer end of the inner tube. The connecting mount is soft and bendable, is securely mounted around the disk segment and has a bottom end, a top end, a middle segment and a flange coat. The bottom end is securely mounted around the disk segment and has an inner surface and an air gap formed between the inner surface of the bottom end of the connecting mount and the disk segment. The middle segment is formed between the bottom end and the top end and has a diameter smaller than that of the bottom end and the top end of the connecting mount. The flange coat is formed on the top end of the connecting mount. The connector is securely mounted around the top end of the connecting mount and has a bottom end and a flange formed around the bottom end of the connector and enclosed by the flange coat on the connecting mount.

Other objectives, advantages and novel features of the invention will become more apparent from the following detailed description when taken in conjunction with the accompanying drawings.

DETAILED DESCRIPTION OF PREFERRED EMBODIMENTS

With reference to FIGS. 1 to 5, an inner type tracheostomy tube in accordance with the present invention has an outer tube 10 and an inner cannula 20.

The outer tube 10 has an airway tube 11, an inflatable cuff 12, an inflating tube 13, a neck mount 14 and a holding mount 15.

The airway tube 11 may be a hard tube and has an inner end, an outer end and an external surface. The inflatable cuff 12 is mounted around the external surface near the inner end of the airway tube 11, is inflated to form a seal in a patient's neck for mechanical breathing, and is totally deflated when the outer tube 10 is inserted into or withdrawn from the patient's trachea. The inflating tube 13 is connected to and communicates with the inflatable cuff 12 to inflate or deflate the inflatable cuff 12.

The neck mount 14 may be an annular hard board, is securely mounted around the external surface of the airway tube 11 near the outer end of the airway tube 11 and has a top, two sides and two neck plates 141. The neck plates 141 are elongated and are respectively formed on and protrude from the sides of the neck mount 14 to allow a cord or strap to be connected to the neck plates 141 and are mounted around the patient's neck to hold the neck plates 141 in place and hold the outer tube 10 securely in the neck of the patient.

The holding mount 15 is formed on the neck mount 14 around the outer end of the airway tube 11 and has a holding ring 151 and two holding arms 152. The holding ring 151 is formed on the top of the neck mount 14 around the outer end of the airway tube 11 and has an external surface and a top. The holding arms 152 are formed oppositely on the external surface of the holding ring 151 and protrude from the top of the holding ring 151, and each holding arm 152 has a bottom, a top, an inner face, a holding recess 153 and an opening 154. The bottoms of the holding arms 152 are formed on the external surface of the holding ring 151 and respectively abut the neck plates 141 of the neck mount 14. The tops of the holding arms 152 extend above the top of the holding ring 151.

The holding recesses 153 may be rectangular and are respectively formed in the inner faces of the holding arms 152 between the tops of the holding ring 151 and the holding arms 152, and each holding recess 153 has a width. The openings 154 are respectively formed through the tops of the holding arms 152 and respectively communicate with the holding recesses 153 of the holding arms 152, and each opening 154 has a width smaller than the width of the holding recess 153.

The inner cannula 20 is detachably connected to the outer tube 10 and has an inner tube 21, a disk segment 22, two locking tabs 23, a connecting mount 24 and a connector 25.

The inner tube 21 is mounted in the airway tube 11 of the outer tube 10 and has an inner end, an outer end and an external surface. The inner end of the inner tube 21 is mounted in the airway tube 11 near the inner end of the airway tube 11. The outer end of the inner tube 21 extends out of the holding ring 151 of the holding mount 15. The disk segment 22 is formed on the external surface of the inner tube 21 at the outer end of the inner tube 21, abuts the holding ring 151 of the holding mount 15 and has a bottom, a top, an external surface, and an inner surface. The bottom of the disk segment 22 abuts the top of the holding ring 151.

The locking tabs 23 are formed on the external surface of the disk segment 22 from the bottom of the disk segment 22 and protrude from the top of the disk segment 22 and are respectively connected to the holding mans 152 of the holding mount 15. Each locking tab 23 has a shape corresponding to the holding recess 153, a lower end, an upper end, a middle, a locking portion 231, a neck portion 232 and a pressing button 233. The locking portions 231 are respectively formed on the lower ends of the locking tabs 23, are formed on the external surface of the disk segment 22 and are respectively and securely mounted in the holding recesses 153 of the holding arms 152, and each locking portion 231 has a width. The neck portions 232 are respectively formed on the middles of the locking tabs 23, are respectively connected with the locking portions 231 and extend out of the openings 154 of the holding arms 152. Each neck portion 232 has a width smaller than the width of the locking portion 231. The pressing buttons 233 are respectively formed on the upper ends of the locking tabs 23 and are respectively connected with the neck portions 232 above the openings 154 of the holding arms 152.

The connecting mount 24 is soft and bendable, is securely mounted around the disk segment 22 between the locking tabs 23 and has a bottom end, an extension segment 243, a middle segment 242 and a top end. The bottom end of the connecting mount 24 is securely mounted around the disk segment 22 between the locking tabs 23, abuts the external surface of the disk segment 22 and forms an air gap 26 between the inner surface of the bottom end of the connecting mount 24 and the disk segment 22. The extension segment 243 is formed on and protrudes from the inner surface of the bottom end and is inserted into the disk segment 22 and abuts the inner surface of the disk segment 22 to mount the disk segment 22 between the bottom end and the extension segment 243. The middle segment 242 is formed between the bottom end and the top end and has a diameter smaller than that of the bottom end and the top end. The connector 25 is securely mounted around the top end of the connecting mount 24. Preferably, an annular flange 252 is formed around the bottom end of the connector 25, and a flange coat 244 is formed on the top end of the connecting mount 24 and is mounted around and encloses the flange 252 on the connector 25. Accordingly, the connector 25 is mounted on the top end of the connecting mount 24, and the inner surface of the connector 25 is flush with the inner surface of the connecting mount 24. In addition, an annular groove 254 is defined in the bottom end of the connector 25, and an annular wall 246 is formed on and protrudes upward from the top end of the connecting mount 24 and extends into the annular groove 254 in the connector 25. After the connecting mount 24 is combined with the disk segment 22 and the connector 25, a heating, ultrasonic welding or high frequency welding process can be applied to combine the disk segment 22, the connecting mount 24 and the connector 25 securely and firmly with each other to form a single part.

Figure 1:
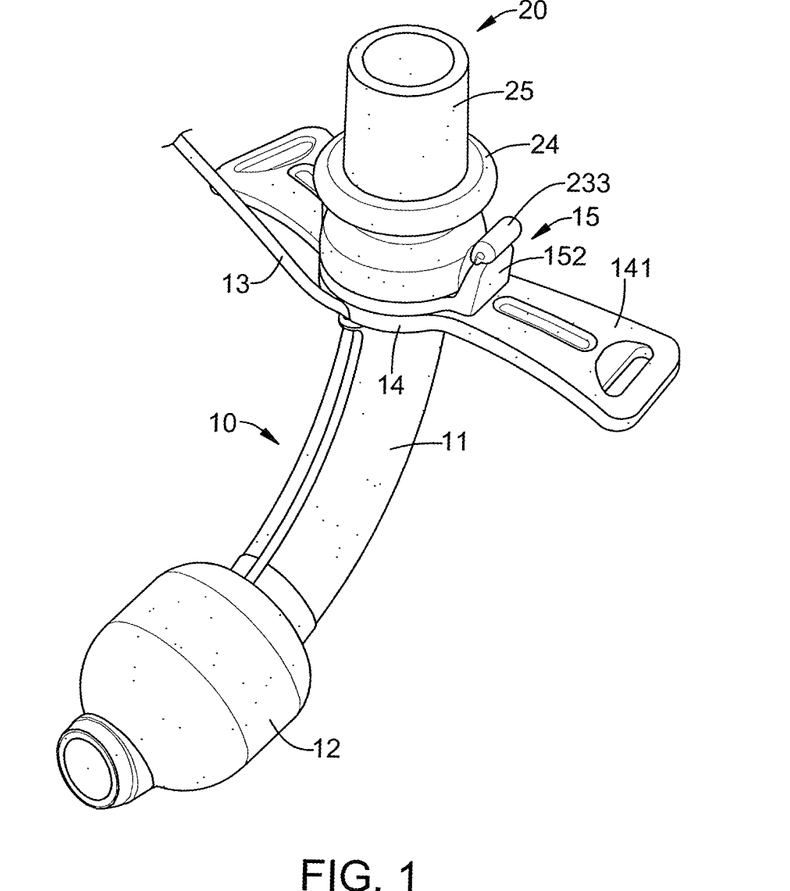
FIG. 1 is a perspective view of an inner type tracheostomy tube in accordance with the present invention.
Figure 5:
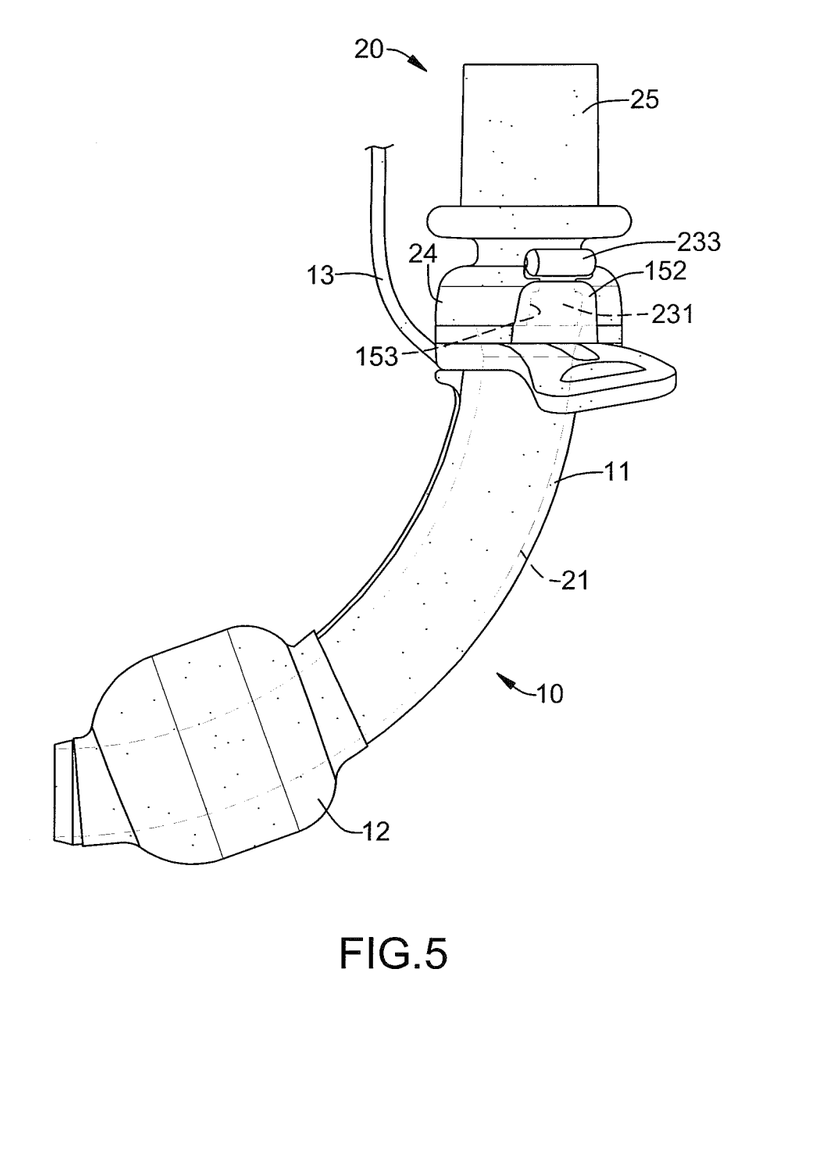
FIG. 5 is a side view of the inner type tracheostomy tube in FIG. 1.
Figure 6:
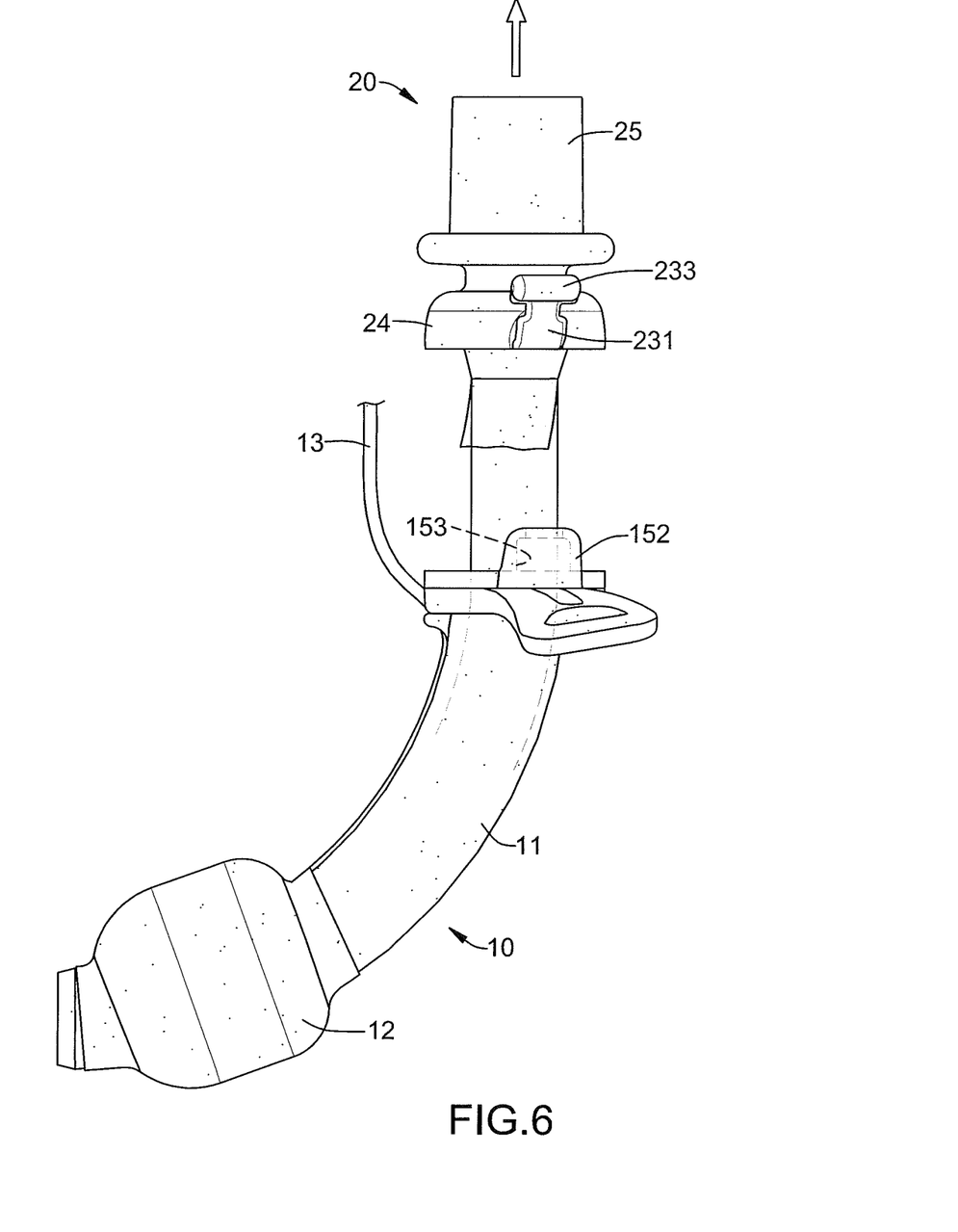
FIG. 6 is an optional side view of an inner cannula of the inner type tracheostomy tube in FIG. 1.

With reference to FIGS. 1 and 5, the airway tube 11 of the outer tube 10 is inserted into a patient's trachea through a stoma defined in the trachea by a surgical operation. A cord or strap can be mounted around the patient's neck to hold the neck plates 141 in place, and the inflatable cuff 12 is inflated through the inflating tube 13 and abuts against an inner surface of the patient's trachea to hold the outer tube 10 securely in the neck of the patient. The connector 25 of the inner cannula 20 is connected to a ventilator or a respiratory tube, so that air can be forced directly into the trachea of the patient through the outer tube 10 and the inner cannula 20 of the inner type tracheostomy tube in accordance with the present invention.

With reference to FIGS. 3 to 6, when the inner cannula 20 is needed to change, the pressing buttons 233 of the locking tabs 23 are pressed to separate the locking portions 231 of the locking tabs 23 respectively from the holding recesses 153 of the holding arms 152. Then, the inner tube. 21 of the inner cannula 20 can be pulled out of the airway tube 11 of the outer tube 10 by pulling the pressing buttons 233 of the locking tabs 23, and a new inner cannula 20 can be inserted and held with the outer tube 10. Accordingly, to change an inner cannula 20 with a new one is convenient and easy.

Figure 2:
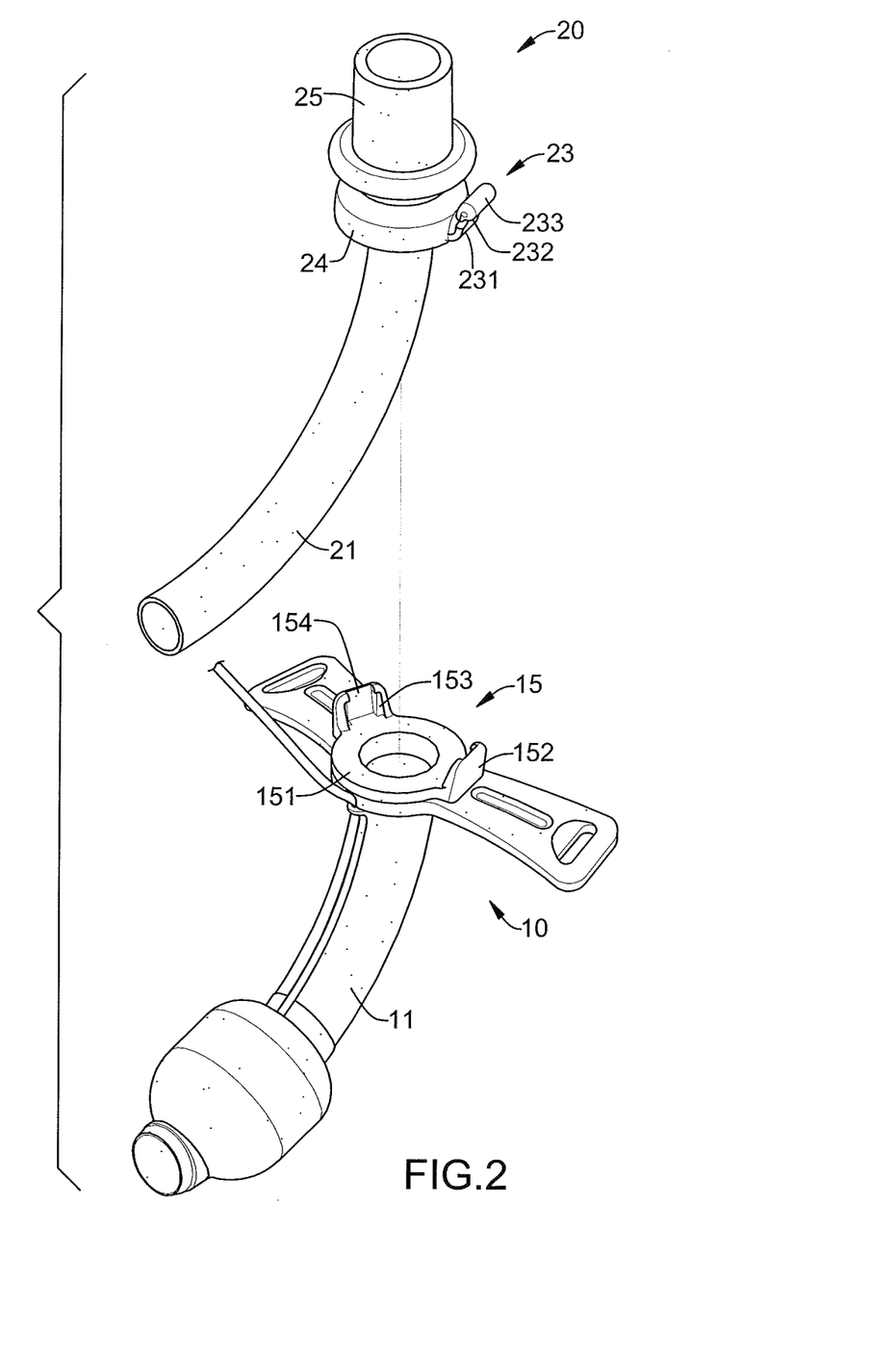
FIG. 2 is an exploded perspective view of the inner type tracheostomy tube in FIG. 1.
Figure 3:
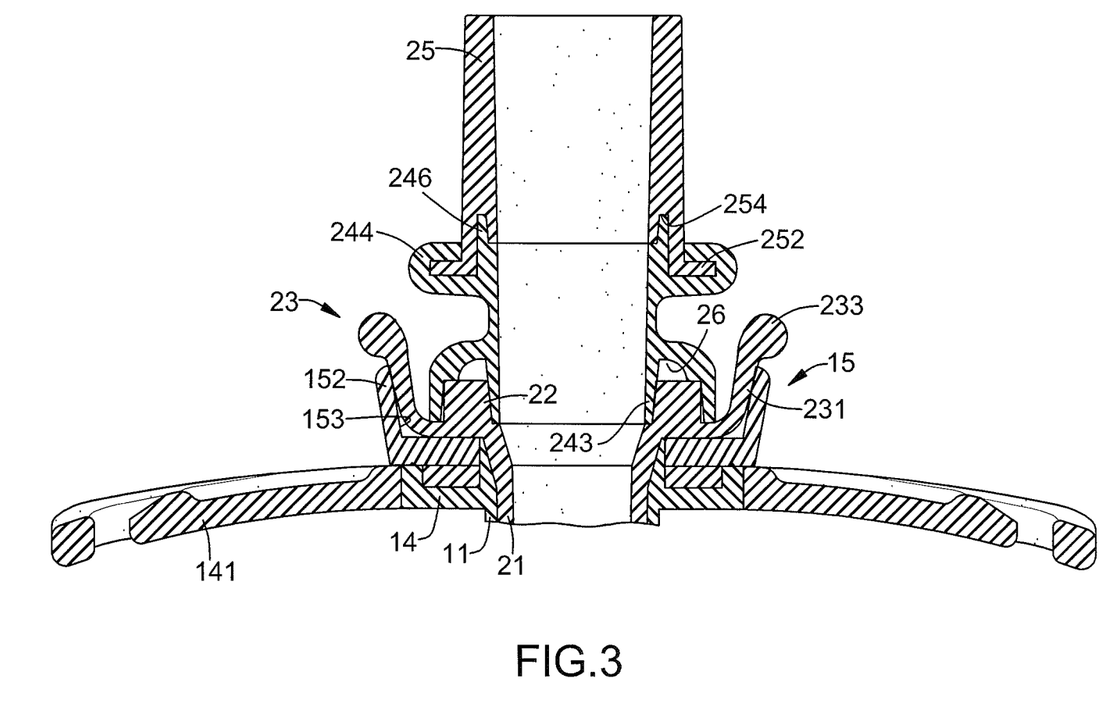
FIG. 3 is an enlarged cross sectional side view of the inner type tracheostomy tube in FIG. 1.
Figure 4:
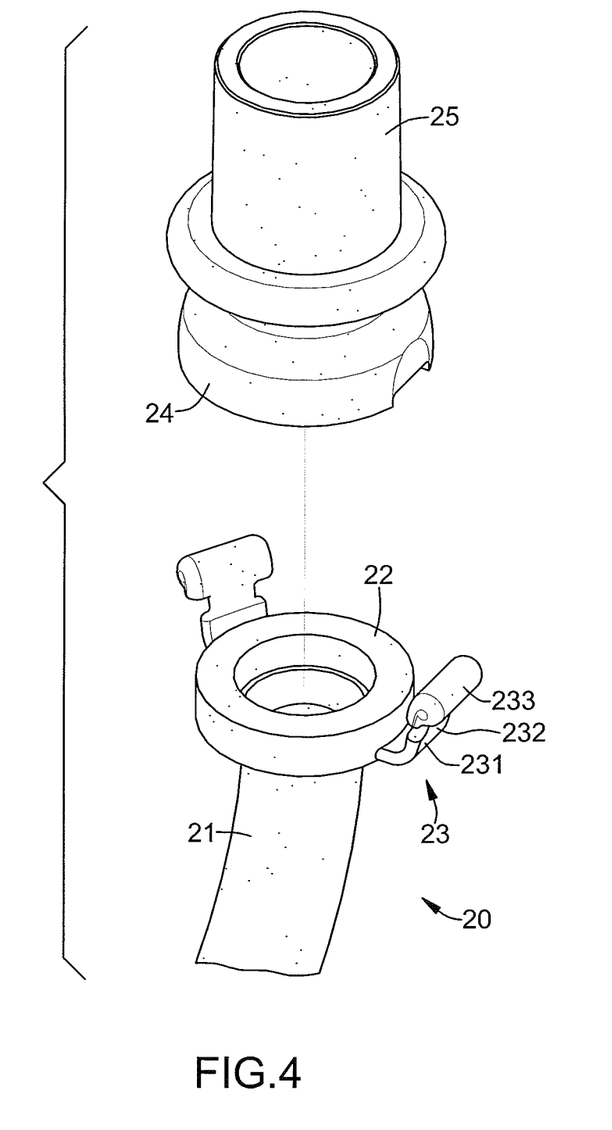
FIG. 4 is an enlarged exploded perspective view of the inner type tracheostomy tube in FIG. 1.

With further reference to FIG. 2, the locking portions 231 of the locking tabs 23 are respectively and securely mounted in the holding recesses 153 of the holding arms 152. This can make the holding arms 152 mounting around the locking tabs 23 prevent dirt from accumulating on the locking tabs 23 and to avoid the patient knocking the locking tabs 23 of the inner cannula 20 to separate the inner cannula 20 from the outer tube 10, and this is clean and safe to use.

Figure 7:
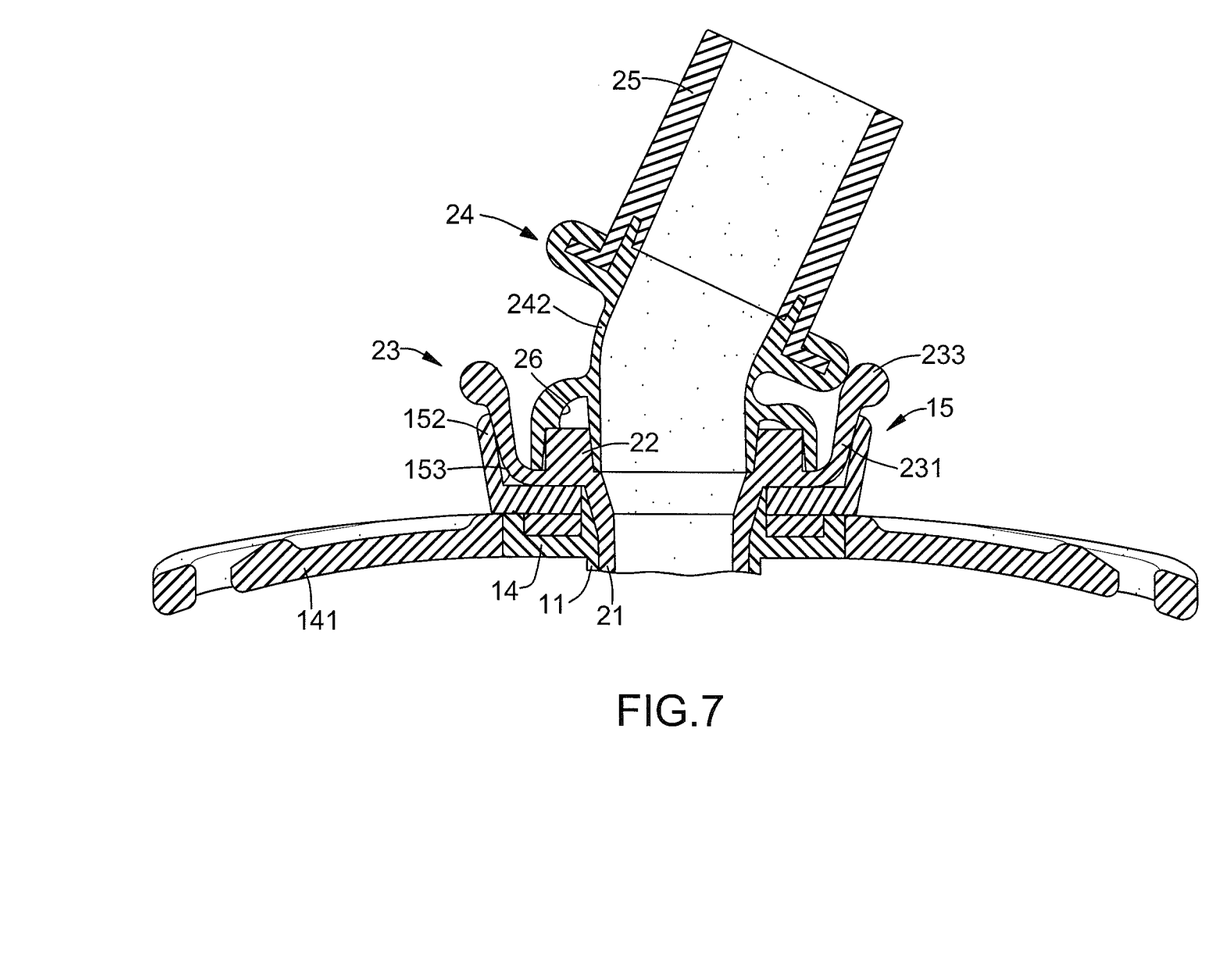
FIG. 7 is an enlarged operational cross sectional side view of the inner type tracheostomy tube in FIG. 1.

With reference to FIG. 7, because the connecting mount 24 is soft, the connecting mount 24 is bendable. When the patient on who the inner type tracheostomy tube is attached is moving or turns the body, the connecting mount 24 may be bent and deformed to form an angle between the connector 25 and the inner tube 21. Accordingly, the ventilator or the respiratory tube that is connected to the connector 25 may not influence the movement of the patient and may not cause discomfort to the patient.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:
1. An inner type tracheostomy tube comprising
an outer tube having
an airway tube having an inner end;
an outer end; and
an external surface;
an inflatable cuff mounted around the external surface at the inner end of the airway tube;
an inflating tube connected to and communicating with the inflatable cuff to inflate or deflate the inflatable cuff;
an inner cannula detachably connected to the outer tube and having
an inner tube mounted in the airway tube of the outer tube and having
an inner end mounted in the airway tube at the inner end of the airway tube;
an outer end; and
an external surface;
a disk segment being annular, formed on the external surface of the inner tube at the outer end of the inner tube and having an external surface and an inner surface;
a connecting mount being bendable, mounted around the disk segment and having
a bottom end mounted around the disk segment, abutting the external surface of the disk segment and having an inner surface and an annular air gap formed between the inner surface of the bottom end of the connecting mount and the disk segment;
an extension segment formed on and protruding from the inner surface of the bottom end, inserted into the disk segment and abutting the inner surface of the disk segment to mount the disk segment between the bottom end and the extension segment;
a top end;
a middle segment formed between the bottom end and the top end and having a diameter smaller than that of the bottom end and the top end of the connecting mount; and
a flange coat formed on the top end of the connecting mount; and
a connector mounted around the top end of the connecting mount and having
a bottom end; and
a flange formed around the bottom end of the connector and enclosed by the flange coat on the connecting mount.

2. The inner type tracheostomy tube as claimed in claim 1, wherein
the outer tube further has
a neck mount mounted around the external surface of the airway tube at the outer end of the airway tube and having
a top; and
two sides; and
a holding mount formed on the neck mount around the outer end of the airway tube and having
a holding ring formed on the top of the neck mount around the outer end of the airway tube and having
an external surface; and
a top; and
two holding arms formed oppositely on the external surface of the holding ring and protruding from the top of the holding ring, and each holding arm having
a bottom formed on the external surface of the holding ring;
a top extending above the top of the holding ring;
an inner face; and
a holding recess formed in the inner face of the holding arm between the top of the holding ring and the holding arm and having a shape and a width; and
the inner cannula further has
two locking tabs formed on an external surface of the disk segment from a bottom of the disk segment and protruding from a top of the disk segment and respectively connected to the holding arms of the holding mount, and each locking tab having
a shape corresponding to a shape of the holding recess in a corresponding holding arm;
a lower end;
an upper end;
a middle;
a locking portion formed on the lower end of the locking tab, formed on the external surface of the disk segment and securely mounted in the holding recess of the corresponding holding arm and having a width; and
a pressing button formed on the upper end of the locking tab above the corresponding holding arm; and
the bottom of the disk segment abuts the top of the holding ring.

3. The inner type tracheostomy tube as claimed in claim 2, wherein
the holding recess of each of the two holding arms is rectangular;
each holding arm has an opening formed through the top of the holding arm, communicating with the holding recess of the holding arm and having a width smaller than the width of the holding recess of the holding arm;
each locking tab has a neck portion formed on the middle of the locking tab, is connected with the locking portion of the locking tab and extending out of the opening of the corresponding holding arm and having a width smaller than the width of the locking portion of the locking tab; and
the pressing button of each of the two locking tabs is connected with a corresponding neck portion above the opening of a corresponding holding arm.

4. The inner type tracheostomy tube as claimed in claim 3, wherein
the neck mount is an annular board and has two neck plates being elongated and respectively formed on and protruding from the sides of the neck mount; and
the bottoms of the holding arms respectively abut the neck plates of the neck mount.

5. The inner type tracheostomy tube as claimed in claim 2, wherein
the neck mount is an annular board and has two neck plates being elongated and respectively formed on and protruding from the sides of the neck mount; and
the bottoms of the holding arms respectively abut the neck plates of the neck mount.

6. The inner type tracheostomy tube as claimed in claim 1, wherein the connector has an inner surface being flush with the inner surface of the connecting mount.

7. A cannula comprising
a tube having
an inner end;
an outer end; and
an external surface;

a disk segment being annular, formed on the external surface of the tube at the outer end of the tube and having an external surface and an inner surface;

a connecting mount being bendable, mounted around the disk segment and having
- a bottom end mounted around the disk segment, abutting the external surface of the disk segment and having an inner surface and an annular air gap formed between the inner surface of the bottom end of the connecting mount and the disk segment;
- an extension segment formed on and protruding from the inner surface of the bottom end, inserted into the disk segment and abutting the inner surface of the disk segment to mount the disk segment between the bottom end and the extension segment;
- a top end;
- a middle segment formed between the bottom end and the top end and having a diameter smaller than that of the bottom end and the top end of the connecting mount; and
- a flange coat formed on the top end of the connecting mount; and a connector mounted around the top end of the connecting mount and having
- a bottom end; and
- a flange formed around the bottom end of the connector and enclosed by the flange coat on the connecting mount.

8. The cannula as claimed in claim 7, wherein the connector has an inner surface being flush with the inner surface of the connecting mount.

9. The cannula as claimed in claim 7, wherein the connecting mount is separately formed from the disk material and of a material softer than that of the disk segment, wherein the external and inner surfaces extend axially with the external surface having a greater radial extent than the inner surface, with the air gap having a radial extent less than the external surface; wherein the connector is separately formed from the connecting mount, and wherein the flange coat includes a radially extending annular portion integrally extending outwardly from the top end, an axially extending annular portion integrally extending from an outer edge of the radial extending annular portion, and a lip radially extending inward from the axially extending annular portion opposite to the axially extending annular portion and towards but spaced from the top end, with the flange located axially between the radially extending annular portion and the lip and the bottom end of the connector located intermediate the top end of the connecting mount and the lip.

10. The cannula as claimed in claim 9, wherein the extension segment includes an annular wall formed on and protruding upward from the top end of the connecting mount; wherein the connector includes an annular groove defined in the bottom end of the connector; wherein the annular wall of the connecting mount extends into the annular groove of the connector; and wherein the connecting mount is bendable.

* * * * *